United States Patent
Brown (10) Patent No.: US 9,675,487 B2
(45) Date of Patent: Jun. 13, 2017

(54) PROSTHESIS DEPLOYMENT SYSTEM FOR VASCULAR REPAIR

(75) Inventor: Elizabeth M. Brown, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 270 days.

(21) Appl. No.: 12/948,118

(22) Filed: Nov. 17, 2010

(65) Prior Publication Data

US 2012/0123511 A1 May 17, 2012

(51) Int. Cl.
| | |
|---|---|
| A61F 2/06 | (2013.01) |
| A61F 2/97 | (2013.01) |
| A61F 2/95 | (2013.01) |
| A61F 2/07 | (2013.01) |
| A61F 2/966 | (2013.01) |

(52) U.S. Cl.
CPC .......... *A61F 2/97* (2013.01); *A61F 2/064* (2013.01); *A61F 2/95* (2013.01); *A61F 2/07* (2013.01); *A61F 2002/9517* (2013.01); *A61F 2002/9665* (2013.01)

(58) Field of Classification Search
CPC .... A61F 2/95; A61F 2/97; A61F 2/064; A61F 2002/9665; A61F 2/07
USPC ........................................ 623/1.11, 1.12, 1.2
See application file for complete search history.

(56) References Cited

U.S. PATENT DOCUMENTS

| | | | |
|---|---|---|---|
| 4,306,562 A * | 12/1981 | Osborne ................ | 604/523 |
| 4,581,025 A | 4/1986 | Timmermans ........... | 604/264 |
| 5,320,602 A | 6/1994 | Karpiel ................... | 604/54 |
| 5,380,304 A | 1/1995 | Parker .................... | 604/282 |
| 5,591,226 A * | 1/1997 | Trerotola et al. ........ | 623/1.12 |
| 5,647,857 A | 7/1997 | Anderson et al. ........ | 604/264 |
| 5,772,669 A | 6/1998 | Vrba | |

(Continued)

FOREIGN PATENT DOCUMENTS

| | | | | |
|---|---|---|---|---|
| EP | 0775470 A1 | 5/1997 | ........... | A61F 2/06 |
| EP | 1 637 176 A1 | 3/2006 | | |

(Continued)

OTHER PUBLICATIONS

Communication pursuant to Article 94(3) EPC for application No. 11 770 613.5, dated Jul. 21, 2015, 6 pp.

(Continued)

*Primary Examiner* — Richard Louis
(74) *Attorney, Agent, or Firm* — Brinks Gilson & Lione (57) ABSTRACT

A deployment system for vascular repair of a transected body vessel is provided. The system can include a prosthesis, an inner sheath, and an outer sheath. The inner sheath can be configured to selectively retain a first portion of the prosthesis in the compressed configuration, leaving a remaining portion of the prosthesis uncovered by the inner sheath. The outer sheath can be configured to retain the remaining portion of prosthesis in the compressed configuration and the first portion of the prosthesis within the inner sheath. The outer sheath is removable from the prosthesis to allow an expansion of the remaining portion of the prosthesis to the expanded configuration at a first opening in the transected vessel. The inner sheath is removable from the prosthesis first portion to allow an independent expansion of the first portion to the expanded configuration at a second opening in the transected vessel.

26 Claims, 5 Drawing Sheets

(56) References Cited

U.S. PATENT DOCUMENTS

| | | | |
|---|---|---|---|
| 6,206,931 B1 | 3/2001 | Cook et al. | 623/23.75 |
| 6,241,758 B1* | 6/2001 | Cox | 623/1.11 |
| 6,432,127 B1 | 8/2002 | Kim et al. | 623/1.11 |
| 6,447,540 B1 | 9/2002 | Fontaine et al. | 623/1.12 |
| 6,562,049 B1 | 5/2003 | Norlander et al. | 606/108 |
| 6,676,666 B2 | 1/2004 | Vrba et al. | 606/108 |
| 6,692,464 B2 | 2/2004 | Graf | 604/160 |
| 6,712,791 B2 | 3/2004 | Lui et al. | 604/167.04 |
| 6,758,854 B1* | 7/2004 | Butler et al. | 606/194 |
| 6,827,731 B2 | 12/2004 | Armstrong et al. | 623/1.12 |
| 6,939,337 B2 | 9/2005 | Parker et al. | 604/528 |
| 7,244,444 B2 | 7/2007 | Bates | 424/423 |
| 7,413,573 B2 | 8/2008 | Hartley et al. | 623/1.13 |
| 7,691,140 B2 | 4/2010 | Bates et al. | 623/1.13 |
| 2002/0099431 A1* | 7/2002 | Armstrong et al. | 623/1.11 |
| 2003/0153935 A1* | 8/2003 | Mialhe | 606/157 |
| 2003/0233115 A1* | 12/2003 | Eversull et al. | 606/194 |
| 2004/0098081 A1* | 5/2004 | Landreville et al. | 623/1.11 |
| 2004/0249433 A1* | 12/2004 | Freitag | 623/1.11 |
| 2006/0235501 A1* | 10/2006 | Igaki | A61F 2/958 |
| | | | 623/1.11 |
| 2007/0027526 A1* | 2/2007 | Demetriades et al. | 623/1.13 |
| 2007/0198077 A1* | 8/2007 | Cully | A61F 2/958 |
| | | | 623/1.12 |
| 2007/0225659 A1* | 9/2007 | Melsheimer | 604/264 |
| 2008/0221659 A1* | 9/2008 | Hartley et al. | 623/1.13 |
| 2008/0288042 A1* | 11/2008 | Purdy et al. | 623/1.11 |
| 2009/0112237 A1 | 4/2009 | Paul, Jr. et al. | 606/155 |
| 2009/0319022 A1 | 12/2009 | Hartley et al. | |
| 2010/0324653 A1* | 12/2010 | Rubenstein et al. | 623/1.15 |

FOREIGN PATENT DOCUMENTS

| | | | |
|---|---|---|---|
| FR | 2885794 A1 | 11/2006 | A61F 2/84 |
| JP | 2009-502343 | 1/2009 | |
| JP | 2009-523565 | 6/2009 | |
| WO | WO 2004/103450 A1 | 12/2004 | |
| WO | WO 2007/016166 A2 | 2/2007 | |
| WO | WO 2007/084762 A2 | 7/2007 | |

OTHER PUBLICATIONS

Office action from Japan Patent Office for application No. 2013-539843, with English translation, 6 pp.

* cited by examiner

PROSTHESIS DEPLOYMENT SYSTEM FOR VASCULAR REPAIR

BACKGROUND

The present disclosure relates generally to medical prosthesis deployment systems for vascular repair. More particularly, the present disclosure relates to a deployment system for a prosthesis to repair a transected body vessel for gaining hemostasis during emergency medical procedures.

Trauma physicians frequently encounter patients having traumatic injury to a body vessel, such as lacerated vessels or even transected vessels, resulting from gunshots, knife wounds, motor vehicle accidents, explosions, etc. Significant damage to a body vessel may expose a patient to deleterious conditions such as the loss of a limb, loss of function of a limb, increased risk of stroke, impairment of neurological functions, and compartment syndrome, among others. Particularly severe cases of vascular injury and blood loss may even result in death. In such severe situations, the immediate goal is to obtain hemostasis while maintaining perfusion of adequate blood flow to critical organs, such as the brain, liver, kidneys, and heart.

Examples of treatment that are commonly performed by trauma physicians to treat body vessel injuries include clamping the vessel with a hemostat, use of a balloon tamponade, ligation of the damaged vessel at or near the site of injury, or the insertion of one or more temporary shunts. However, conventional surgical repair is generally difficult with such actively bleeding, moribund patients. In many instances, there is simply not enough time to repair the body vessel adequately by re-approximating and suturing the body vessel. In many situations, the trauma physician will simply insert a temporary shunt (such as a Pruitt-Inahara Shunt) into the vessel. However, use of temporary shunts has been linked to the formation of clots. This may require returning the patient to the operating room for treatment and removal of the clots, often within about 36 to 48 hours of the original repair. Since shunts are generally placed as a temporary measure to restore blood flow and stop excessive blood loss, the shunt is typically removed when the patient has stabilized (generally a few days later) by a specialized vascular surgeon. After removal, the vascular surgeon will replace the shunt with a vascular graft, such as a fabric graft that is sewn into place. Ligation of the damaged blood vessel may result in muscle necrosis, loss of muscle function, or a potential limb loss or death.

Due to the nature of the body vessel injury that may be encountered, the use of shunts, repairing and/or ligating of a blood vessel often requires that such treatments be rapidly performed at great speed, and with a high degree of physician skill. Such treatments may occupy an undue amount of time and attention of the trauma physician at a time when other pressing issues regarding the patient's treatment require immediate attention. In addition, since the level of particularized skill required may exceed that possessed by the typical trauma physician, particularly traumatic episodes may require the skills of a physician specially trained to address the particular trauma, such as a vascular trauma, and to stabilize the patient in the best manner possible under the circumstances of the case.

Some open surgical techniques utilize sutures to affix damaged tissue portions surrounding fittings that have been deployed with the vessel, which requires the trauma physician to take time to tie the sutures properly. Although in modern medicine sutures can be tied in relatively rapid fashion, any step in a repair process that occupies physician time in an emergency situation is potentially problematic. In addition, the use of sutures to affix the vessel to the fitting compresses the tissue of the vessel against the fitting. Compression of tissue may increase the risk of necrosis of the portion of the vessel tissue on the side of the suture remote from the blood supply. When present, necrosis of this portion of the vessel tissue may result in the tissue separating at the point of the sutures. In this event, the connection between the vessel and the fitting may eventually become weakened and subject to failure. If the connection fails, the device may disengage from the vessel. Therefore, efforts continue to develop techniques that reduce the physician time required for such techniques, so that this time can be spent on other potentially life-saving measures.

U.S. Patent Publication No. 2009/0112237 to Paul, Jr. et al., which is incorporated herein by reference in its entirety, discloses examples of vascular conduits and delivery systems for open surgical placement. One such delivery system is depicted in FIG. 17A, which can include a tubular member, a dilator tip, a proximal handle, and a controller for manipulating the dilator tip. The delivery system may be configured to move the dilator tip axially relative to the tubular member between an extended position and a retracted position. At the retracted position, the dilator tip may be positioned around a distal portion of the vascular conduit, and at the extended position, the dilator tip can be positioned away from contact with the vascular conduit to permit deployment of the vascular conduit into the body vessel. Deployment of the vascular conduit into ends of a transected vessel using the delivery system is shown in FIGS. 23A-23E of the published application. As shown in FIGS. 23B and 23C, the dilator tip and portions of the vascular conduit disposed on the delivery system are positioned within the ends of the transected vessel. Once in the vessel, the dilator tip can be moved to the extended portion to permit anchoring of the vascular conduit to walls of the vessel.

Trauma physicians generally are familiar with using a stent delivery catheter and a splittable introducer sheath. Accordingly, when encountering patients having traumatic injury to a body vessel, it would be desirable for the trauma physician to deliver a medical prosthesis with a deployment system that operates similar to conventional stent delivery catheters and splittable sheaths to repair an injured body vessel. Thus, it would be desirable to provide a prosthesis deployment system for use in repair of an injured body vessel, such as an artery or a vein, (and in particular a transected vessel) during emergency open surgery in a manner that is time effective, that addresses the trauma at hand to the extent possible, and that utilizes techniques that may be readily practiced by an trauma physician.

SUMMARY

Provided herein is one embodiment of a deployment system for repair of a body vessel. The system can include a prosthesis, an inner sheath, and an outer sheath. The prosthesis can be radially movable between a compressed configuration and an expanded configuration. The inner sheath can be configured to selectively retain a first portion of the prosthesis in the compressed configuration, leaving a remaining portion of the prosthesis uncovered by the inner sheath. The outer sheath can have a lumen extending therethrough configured to receive the prosthesis in the compressed configuration. The outer sheath can have a delivery position and a deployed position. In the delivery position, the outer sheath can retain the remaining portion of prosthesis in the compressed configuration and the first portion of the prosthesis within the inner sheath. In the deployed position, the outer sheath can be removed from the prosthesis to allow an expansion of the remaining portion of the prosthesis to the expanded configuration. The inner sheath is removable from the first portion of the prosthesis to allow an expansion of the first portion of the prosthesis to the expanded configuration, independent to the expansion of the remaining portion. In one example, the inner sheath is a splittable sheath.

In another embodiment, a deployment system for repair of a transected body vessel having two vessel end openings is provided. The system can include self-expanding prosthesis, an inner sheath, and an outer sheath. The inner sheath can be disposed around only an inner sheath portion of the prosthesis to leave a remaining portion of the prosthesis uncovered by the inner sheath. The inner sheath can be configured to selectively retain the inner sheath portion of the prosthesis in the compressed configuration. The outer sheath can be disposed around the prosthesis to retain the remaining portion of the prosthesis in the compressed configuration and to surround the inner sheath with the inner sheath portion of the prosthesis. A distal portion of the outer sheath is sized to fit within a first of the vessel end openings. The outer sheath is removable from the prosthesis to allow a first expansion of the remaining portion of the prosthesis to the expanded configuration at the first of the vessel end openings of the transected body vessel. At least a partial portion of the inner sheath is sized to fit within a second of the vessel end openings. The inner sheath is removable from the inner sheath portion of the prosthesis to allow a second expansion, independent to the first expansion, of the inner sheath portion to the expanded configuration at the second of the vessel end openings of the transected body vessel. The outer sheath may be configured to be removed from the prosthesis in a first direction toward an intermediate portion of the prosthesis away from the prosthesis. The inner sheath may be configured to be removed from the inner sheath portion of the prosthesis in a second direction, opposite the first direction, toward the intermediate portion of the prosthesis, whereby radial expansion of the intermediate portion of the prosthesis is subsequent to radial expansion of the proximal and distal ends of the prosthesis.

A method of delivering a prosthesis for intraoperative repair of a transected body vessel is also provided. The method can include one or more of the following steps. A deployment system can be provided including a prosthesis having a proximal end and a distal end, and being radially movable between a compressed configuration and an expanded configuration, an inner sheath configured to selectively retain a first portion of the prosthesis in the compressed configuration, leaving a remaining portion of the prosthesis uncovered by the inner sheath, an outer sheath having a lumen extending therethrough configured to receive the prosthesis in the compressed configuration, the outer sheath retaining the remaining portion of prosthesis in the compressed configuration and the first portion of the prosthesis with the inner sheath. A distal end of the outer sheath of the deployment system can be inserted into a first end opening of the transected body vessel, and positioned so that a length of the remaining portion of the prosthesis is within a first vessel portion. The outer sheath can be removed from the prosthesis to allow an expansion of the remaining portion of the prosthesis to the expanded configuration so that the remaining portion of prosthesis engages along a vessel wall of the first vessel portion. A length of the first portion of the prosthesis with the inner sheath can be inserted into a second end opening of the transected body vessel. The inner sheath can be removed from the first portion of the prosthesis to allow an expansion of the first portion of the prosthesis to the expanded configuration so that the first portion engages along a vessel wall of a second vessel portion, and the prosthesis provides a fluid conduit between the first and second vessel portions of the transected body vessel.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The prosthesis delivery systems described herein can be useful for repair of a body vessel, such as a blood vessel, during a medical procedure such as an emergency open surgical procedure. The prosthesis deployment systems can be particularly useful to deliver a prosthesis for repair of a lacerated artery or vein during emergency surgery, and particularly, to obtain hemostasis while maintaining blood perfusion, especially after transection of the body vessel.

Figure 1:
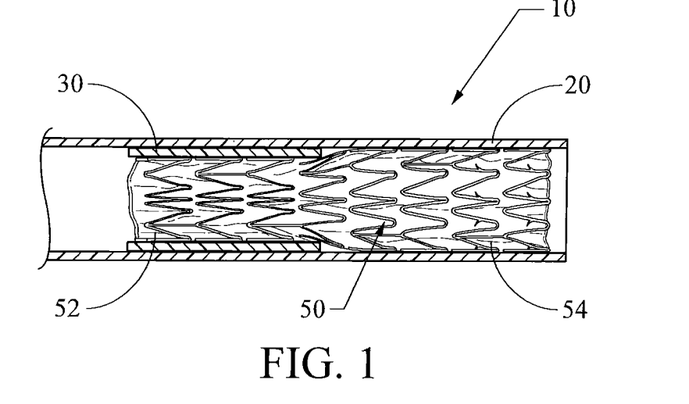
FIG. 1 is a side view of one embodiment of a deployment system for vascular repair of a body vessel.

FIG. 1 depicts one example of a deployment system 10 for vascular repair of a body vessel. Deployment system 10 can include an outer sheath 20, an inner sheath 30, and a prosthesis 50. Deployment system 10 is capable of at least a two-part introduction of prosthesis 50 into the body vessel, as will be described below in further detail. According to the figures, prosthesis 50 has a first end portion 52, and a second end portion 54 at an opposite axial end of the prosthesis from the first end portion. First end portion 52 extends to a proximal end 56 of the prosthesis, and second end portion 54 extends to a distal end 58 of the prosthesis. Inner sheath 30 can directly retain a first end portion 52 of prosthesis 50 in a compressed configuration, and outer sheath 20 can retain the entire prosthesis. That is, outer sheath 20 can directly retain a second end portion 54 of prosthesis 50 in the compressed configuration, as well as the first end portion 52 that is retained by inner sheath 30.

Outer sheath 20 is removable from the prosthesis so that prosthesis 50 is capable of expanding to an expanded configuration for engagement with the body vessel wall. To this end, when outer sheath 20 is removed, the second end portion 54 of prosthesis 50 can expand to the expanded configuration independent to the expansion of the first end portion 52 of prosthesis 50.

Figures 2, 2C:
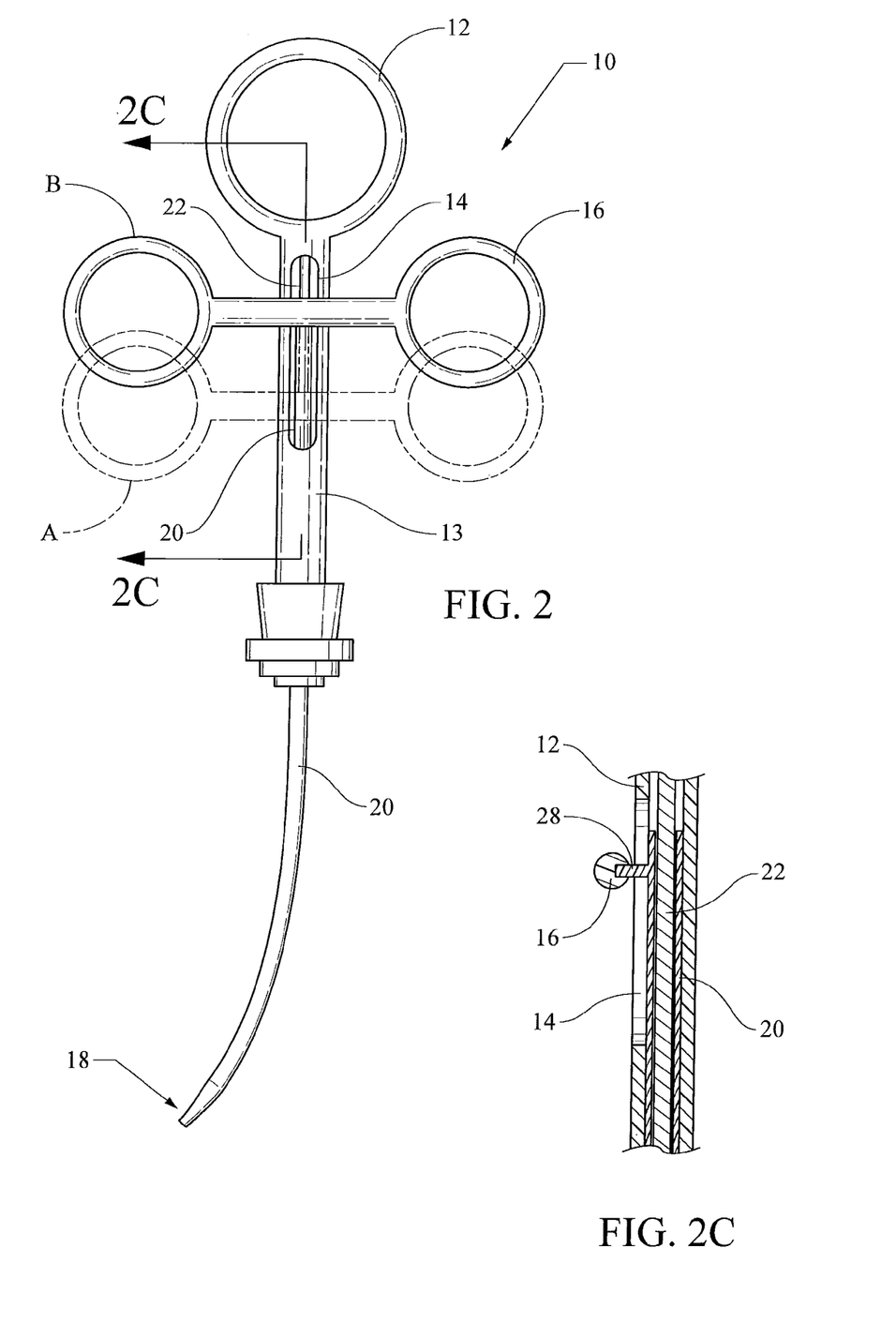
FIG. 2 is a front view of another embodiment of a deployment system for vascular repair of a body vessel.
FIG. 2C is cross-sectional view of a proximal handle of the deployment system of FIG. 2, taken along lines 2C-2C in FIG. 2.
Figure 2A:
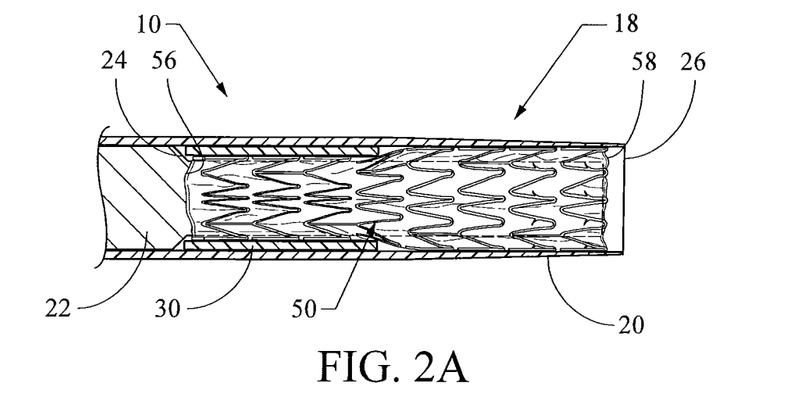
FIG. 2A is a side view of a distal portion of the deployment system of FIG. 2, depicting an outer sheath in a delivery configuration.

According to FIG. 2, deployment system 10 may have a proximal handle 12 that is attached to outer sheath 20 to facilitate removal of the outer sheath from a loaded prosthesis. Proximal handle 12 can be a tubular body 13 and can have a slot 14 and a crossbar member 16 slidably mounted to proximal handle 12 through slot 14. The proximal end of the proximal handle and/or the crossbar member may be configured to receive fingers of an operator, such as rings, for improved grippability and maneuverability. FIG. 2A is an enlarged view of a distal portion 18 of deployment system 10 of FIG. 2, depicting that system 10 may further include an inner shaft 22 disposed within outer sheath 20. Inner shaft 22 can be configured to contact a proximal end 56 of prosthesis 50 when outer sheath 20 is being moved relative to prosthesis 50. For example, inner shaft 22 may further include an enlarged portion 24 sized to contact the prosthesis. Optionally, a blocker sized to contact the prosthesis can be attached to the inner shaft and function in a similar fashion as the enlarged portion 24. Inner shaft 22 may have a portion that further extends distally through the lumen of prosthesis 50, which is shown as dashed lines. To this end, the distal extending portion of the inner shaft is spaced radially from the outer sheath to define an annular lumen for receiving the prosthesis. A distal end 26 of outer sheath 20 can be tapered to facilitate insertion of the system within a body vessel opening. Optionally, an atraumatic tip such as a dilator, conical tip may be attached to the inner shaft to facilitate insertion of the system within the vessel. A guidewire (not shown) may also be used to facilitate trackability of the system within the vessel. Accordingly, the inner shaft, when provided, may include a guidewire lumen extending therethrough for receiving the guidewire.

Figure 2B:
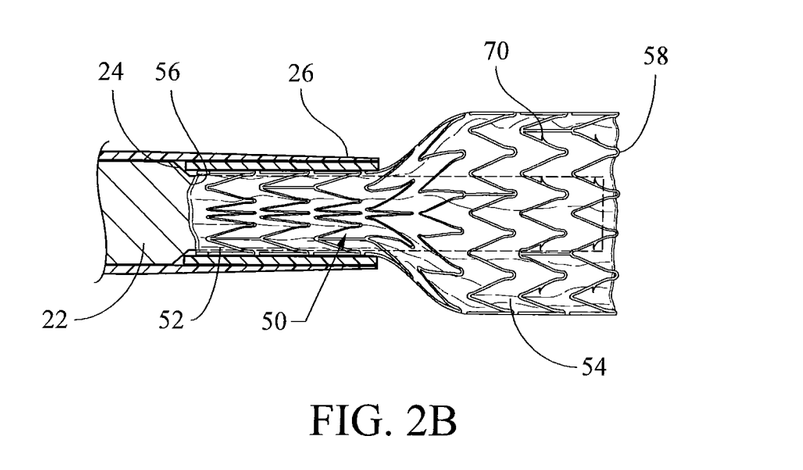
FIG. 2B is a side view of a distal portion of the deployment system of FIG. 2, depicting an outer sheath in a deployed configuration.

Proximal handle 12 can be manipulated by an operator in order to facilitate movement of outer sheath 20 relative to prosthesis 50. FIG. 2C illustrates a partial cross-sectional view of the body of proximal handle 12. In FIG. 2C, crossbar member 16 is directly attached to outer sheath 20, e.g., through a pin 28 that is sized to fit within slot 14. To this end, movement of crossbar member 16 within slot 14, for example between position A and position B, causes movement of outer sheath 20 at distal portion 18 of system as shown in FIGS. 2A-2B, respectively. In other words, sliding crossbar member 16 to position A causes distal end 26 of outer sheath 20 to move in a distal direction to a position to retain the prosthesis as shown in FIG. 2A. Sliding the crossbar member 16 to position B causes distal end 26 of outer sheath 20 to move in a proximal direction to a position where it is removed from the second portion 54 of prosthesis 50, as shown in FIG. 2B, although the outer sheath can be removed entirely from the inner sheath as well. When the outer sheath is in position B, the second portion 54 of prosthesis 50 can move to the expanded configuration, while the first portion 52 of prosthesis 50 can be still retained in the compressed configuration by inner sheath 30. The initial position of the crossbar can initiate at either end of the slot so long as relative movement between the outer sheath and the inner sheath for deployment can be achieved.

Figure 3A:
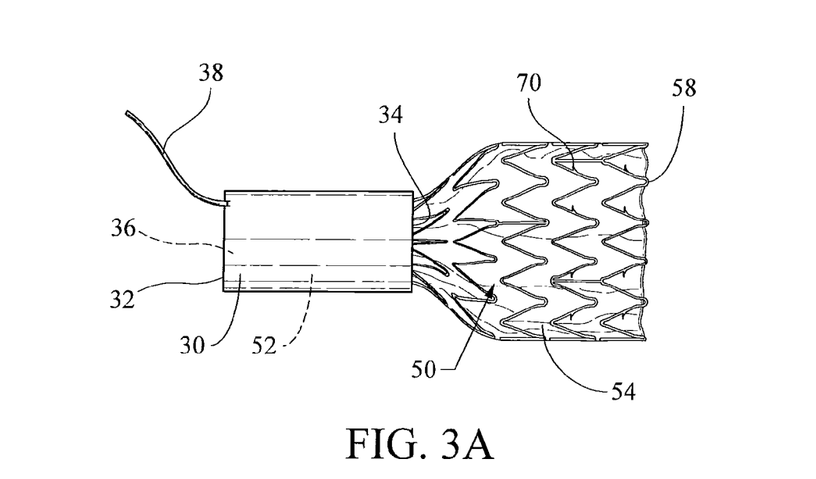
FIG. 3A is a side view of the deployment system of FIG. 2 with the outer sheath completely removed, depicting an inner sheath around a portion of a prosthesis.
Figure 3B:
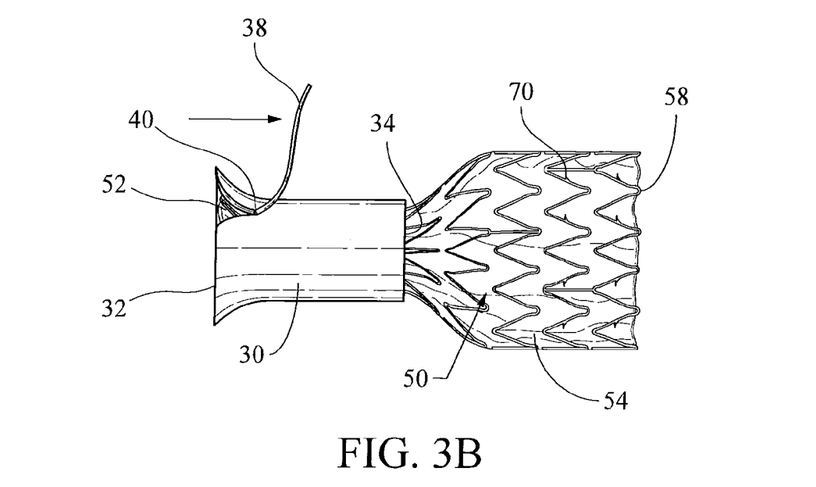
FIG. 3B is a side view of the deployment system of FIG. 2 with the outer sheath completely removed, depicting partial removal of an inner sheath from a prosthesis.

FIG. 3A depicts the outer sheath entirely removed from prosthesis 50 and inner sheath 30. Inner sheath 30 may be a splittable sheath to facilitate removal of the inner sheath from the prosthesis. Inner sheath 30 is preferably configured to be removed from the first portion 52 of prosthesis 50 after removal of outer sheath 20 therefrom. This removal can permit the first portion 52 to move to the expanded configuration, independent to the expansion of the second portion 54 of prosthesis 50. Inner sheath 30 has a proximal end 32 and a distal end 34, and a lumen 36 extending therethrough. Inner sheath 30 may have a handle portion 38 in the form of strip attached to proximal end 32 of inner sheath 30. Handle portion 38 can be discrete from and attached to the inner sheath or formed integrally therewith. Handle portion 38 may comprise a suture, trigger wire, or the like attached to the inner sheath, as appreciated by those skilled in the art. Handle portion 38 can be sized so that the operator can grasp the handle portion from an intermediate portion of the prosthesis, as shown in FIG. 3B. In one example, the handle portion is sized to extend beyond distal end 34 of inner sheath 30. Notches may be formed at the proximal end of the prosthesis on at least one side of the attachment of the handle portion to facilitate splitting there along.

In FIG. 3B, tension applied to handle portion 38 by withdrawing or pulling can cause a split to form in the wall of inner sheath 30 preferably from proximal end 32 of prosthesis 50 toward the distal direction. Preferably, the split is a longitudinal split 40 that is formed along the length of inner sheath 30 between the proximal and distal ends 32, 34, thereby permitting the first portion 52 of prosthesis 50 to begin expansion, as shown by the expanded flared proximal end in FIG. 3B. Handle portion 38 can be pulled until it can be removed from attachment to inner sheath 30 to form a fully split inner sheath. The fully split inner sheath can permit the first portion 52 of prosthesis 50 to fully expand to the expanded configuration, and thereafter the inner sheath can be removed.

Inner sheath 30 can be splittable by use of any well-known means or material that permits the sheath to be separated, preferably longitudinally, along a relatively predictable path. The inner sheath may be separated into two or more portions, thereby opening a fissure along the length that permits its removal from around the prosthesis situated therein. A predetermined split line may be formed in the inner sheath through which the tear or split progresses due to properties of, and/or features incorporated into the sheath material. Preferably, the means for splitting the sheath can withstand being subjected to a curve to the degree required by the particular application without kinking or premature separation. In one example, the inner sheath can comprise a splittable polymer such as molecularly oriented, non-isotropic PTFE that is used to make the PEEL-AWAY® Introducer Sheath (Cook Incorporated, Bloomington, Ind.), which is described in, e.g., U.S. Pat. No. 4,306,562 to Osborne and U.S. Pat. No. 4,581,025 to Timmermans, each of which is incorporated herein by reference in its entirety. In another example, the inner sheath can be made splittable by adding at least one preweakened feature, such as a score line, perforations, or reduced wall thickness regions, extending longitudinally along the length of the sheath. The longitudinal preweakened feature may be included anywhere from one or more orthogonal predetermined split lines to a helical type arrangement that may comprise only a single predetermined split line. The preweakened feature may have inner sheath portions that engage each other with a zipper-like or tongue-and-groove-like interface, or any other splittable connection interface along the contacting lateral edges of the inner sheath portion. Other examples of splittable sheath configurations can be found in U.S. Pat. No. 6,447,540 to Fontaine et al. and U.S. Pat. No. 6,827,731, each of which is incorporated herein by reference in its entirety.

Outer sheath 20 can be constructed from one or more layers. For example, the outer sheath can be extruded from a biocompatible polymer material. In addition, the outer sheath can be formed of multiple layers of at least an outer layer such as a polyether block amide, nylon, polyurethane or the like, a reinforcement layer such as a metal or polymer braid and/or coil, and an inner liner such as PTFE or FEP. One example of an outer sheath is the FLEXOR® Sheath (Cook Incorporated, Bloomington, Ind.), which is described in, e.g., U.S. Pat. No. 5,380,304 to Parker and U.S. Pat. No. 6,939,337 to Parker et al., each of which is incorporated herein by reference in its entirety.

Figure 4:
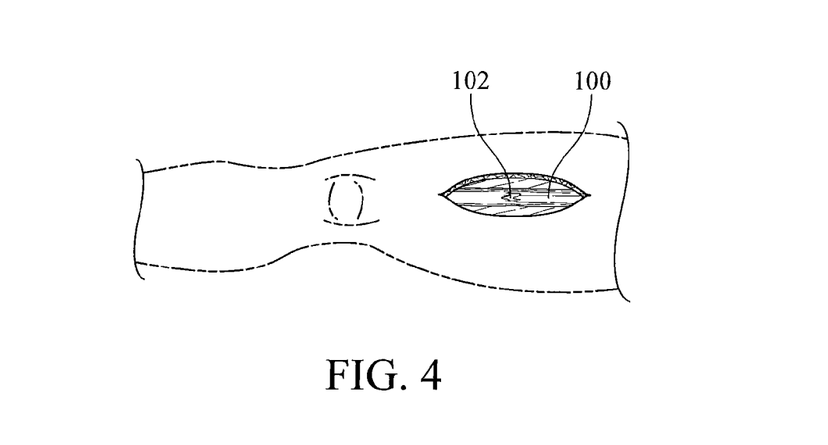
FIG. 4 is a top view of a leg of a patient having a body vessel under trauma.

Prosthesis 50 can be any type of implant, stent, graft or conduit that is used for vascular applications, and an exemplary prosthesis is shown in the figures. The prosthesis can include a generally tubular graft portion and one or more stent structures that are attached to the graft. The prosthesis can be expandable between the radially compressed, delivery configuration that is shown in FIGS. 1 and 2A, to the radially expanded, deployed configuration that is shown in FIG. 4E. The stent structure can attach to an outer surface of the graft so that a lumen of the graft may provide a clear path for fluid flow. The prosthesis can be sized and shaped for suitable placement within a body vessel, such as an artery or vein, and most particularly, for placement at the site of a vascular trauma such as a transected vessel. The stent structure can be any pattern of stent structures in the art that are designed primarily for vascular applications, and can be self-expanding or balloon expandable. Anchoring means 70 can be disposed along any portion of the prosthesis for securely engaging the vessel wall in order to inhibit migration of the prosthesis after deployment or detachment of the vessel wall from the prosthesis. Preferably, the anchoring means are disposed along the two end portions of the prosthesis. Anchoring means 70 can include barbs or various shaped member structures, including fibers, bristles, or outer protruding and penetrable media. Preferably, anchoring means provides vessel fixation to the wall tissue, while avoiding adverse conditions associated with disturbing the vasa vasorum and/or pressure induced necrosis of the medium muscular arteries of the type that may result from tying ligatures circumferentially around a connector or a vascular conduit. For example, anchoring means may be sized and shaped to penetrate the tunica intima, the basement membrane, and partially into the tunica media of a typical body vessel wall, and preferably does not enter the tunica adventitia, and more importantly, do not disturb or otherwise adversely affect the vasa vasorum.

The graft can be a liner that extends at least entirely along the luminal wall of stent structure. The graft can be made of material to inhibit fluid or blood located within the prosthesis lumen from passing through the graft. In other words, fluid flow is urged by the graft to enter into one end and exit out of the end of the prosthesis. The graft can be formed from conventional materials well known in the medical arts. It is preferred that the graft covering have a porosity for sufficient capillarization and be relatively thin as possible (e.g., about 0.005 inches to about 0.010 inches, and preferably about 0.001 to about 0.0035 inches). Examples of pore density and pore size for the graft covering, as well as other types of materials for a graft covering can be found in U.S. Pat. No. 7,244,444 to Bates, which is incorporated herein by reference in its entirety. A particularly preferred material is expanded polytetrafluoroethylene (ePTFE). Other materials that may be suitable in a particular case include, among others, polytetrafluoroethylene, silicone, polyurethane, polyamide (nylon), as well as other flexible biocompatible materials. Graft covering 15 can also be formed from known fabric graft materials such as woven polyester (e.g. DACRON®), or from a bioremodelable material. One exemplary graft material is THORALON® from Thoratec Corporation, Pleasanton, Calif., that can prevent leakage of fluid through the pores of the graft. THORALON® is a polyetherurethane urea blended with a siloxane containing surface modifying additive, and has been demonstrated to provide effective sealing of textile grafts. Another example is polyethylene, and in particular, an ultra-high molecular weight polyethylene (UHMwPE), commercially available as DYNEEMA®. The graft may also include a bioremodelable material that can provide an extracellular matrix that permits, and may even promote, cellular invasion and ingrowth into the material upon implantation. Non-limiting examples of suitable bioremodelable materials include reconstituted or naturally-derived collagenous materials. Suitable collagenous materials may include an extracellular matrix material (ECM) that possesses biotropic properties, such as submucosa, renal capsule membrane, dermal collagen, dura mater, pericardium, fascia lata, serosa, peritoneum or basement membrane layers. Suitable submucosa materials may include, for example, intestinal submucosa, including small intestinal submucosa (SIS), stomach submucosa, urinary bladder submucosa, and uterine submucosa. One non-limiting example of a suitable remodelable material is the SURGISIS® BIODESIGN™, commercially available from Cook Incorporated, Bloomington, Ind. Another suitable remodelable material is the graft prosthesis material described in U.S. Pat. No. 6,206,931 to Cook et al., incorporated herein by reference. The remodelable material can be ECM, SIS, remodelable or collagenous foam, foamed ECM, lyophilized SIS, vacuum pressed SIS, or the like.

The prosthesis described herein can also include a coating of one or more therapeutic agents along a portion of the conduit body and/or the graft coverings. Therapeutic agents for use as biocompatible coatings are well known in the art. Non-limiting examples of suitable bio-active agents that may be applied to the vascular conduit include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Those skilled in the art will appreciate that other bioactive agents may be applied for a particular use. The bioactive agent can be incorporated into, or otherwise applied to, portions of the vascular conduit by any suitable method that permits adequate retention of the agent material and the effectiveness thereof for its intended purpose.

Figure 4A:
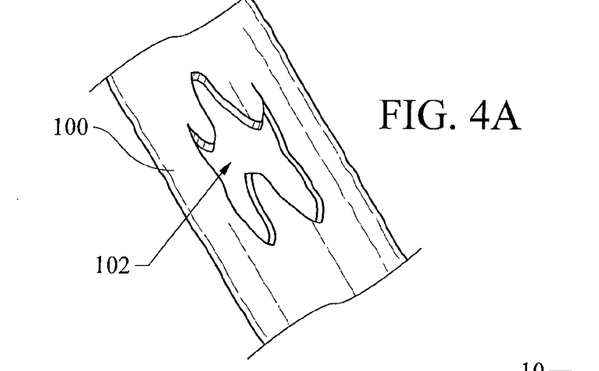
FIGS. 4A-4E are partial views depicting operation of a deployment system.
Figure 4B:
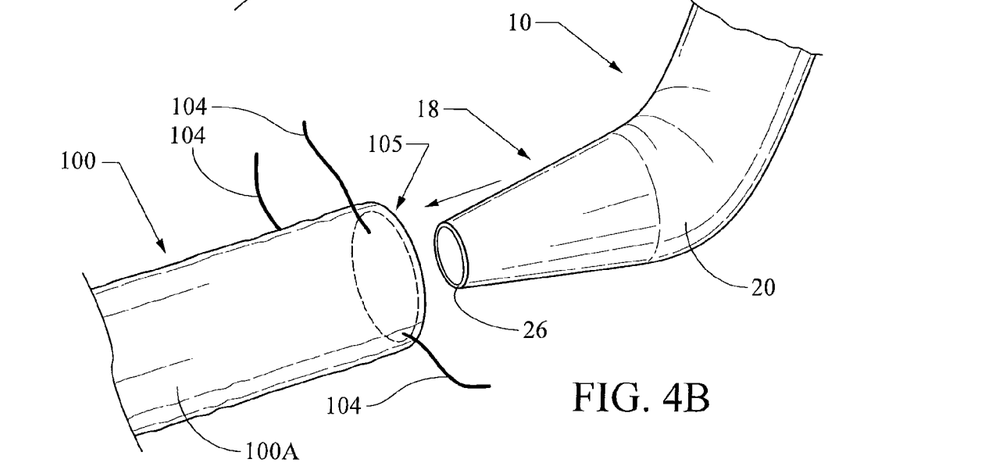
Figure 4C:
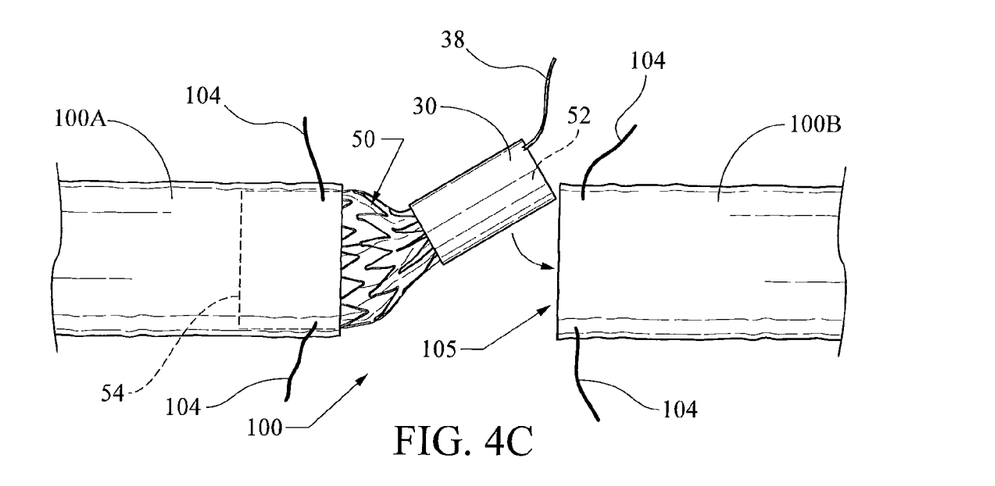
Figure 4D:
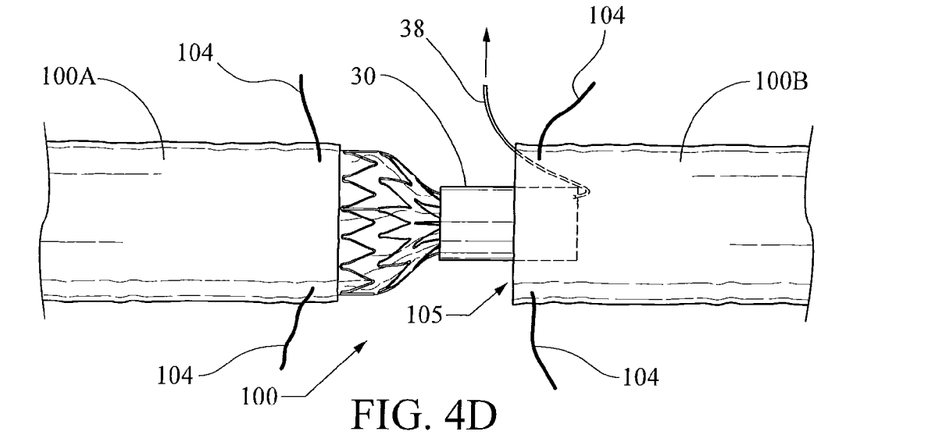
Figure 4E:
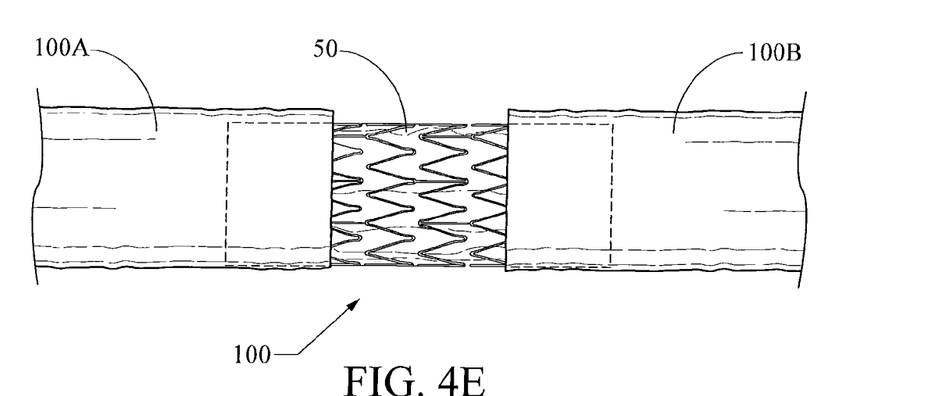

FIGS. 4A-4E illustrate a method of delivering a prosthesis to a transected body vessel. In FIGS. 4 and 4A, a body vessel 100, for example in the leg of a patient, has previously been subjected to a traumatic episode, which results in a portion 102 of blood vessel 100 being torn away or otherwise severely damaged. Pre-surgery preparation has been applied to the leg in order to gain access to the body vessel and the damaged portion thereof. After clamping the blood vessel 100 on both ends of the portion 102 to restrict blood flow temporarily, the blood vessel 100 can be cut or transected into two portions 100A, 100B. The transection may be at the damaged portion 102 of the blood vessel 100 or as far away as necessary from the damaged portion to remove unhealthy vessel or permanently damaged portions of the body vessel. As shown in the figures, sutures 104 can be attached to the end openings 105 of body vessel portions 100A, 100B to keep the portions 100A, 100B fixed in place and to keep the vessel lumen opened to facilitate insertion of a prosthesis with a deployment system. Any number of sutures can be used to retain the end openings 105 in the open position, although triangulation sutures are sufficient, with each suture being about 120 degrees apart from the adjacent suture. A prosthesis is selected to have a radial expanded cross-section and a longitudinal length sufficient to bridge the body vessel portions and radially fit within the body vessel portions.

In FIG. 4B, distal portion 18 of deployment system 10 can be introduced into the end opening 105 of the first portion 100A of transected body vessel 100. Deployment system 10 preferably has the tapered distal end, and can be positioned within the first portion 100A of transected body vessel 100 so that at least a portion of the second portion 54 of prosthesis 50 is within the first portion 100A of the body vessel. In addition, it is desirable for the outer sheath of the deployment system to have a curvature, such as shown in FIG. 2. The curvature can facilitate placement of the prosthesis within the vessel, which the vessel is typically obliquely oriented to the delivery pathway of the deployment system as shown in FIG. 4. In FIG. 4C, outer sheath 20 can be removed from the prosthesis in order to allow expansion of the second portion 54 of prosthesis 50 to the expanded configuration to engage the wall tissue of the first portion 100A of transected body vessel 100. For example, crossbar member 16 in FIG. 2 can moved to position B, thereby causing the outer sheath to be removed from at least the second portion of the prosthesis, such as shown in FIG. 2B. FIG. 4C depicts the second portion 54 of prosthesis 50 deployed within the first portion 100A of the transected body vessel, and first portion 52 of prosthesis 50 is depicted in the compressed configuration within inner sheath 30, which can be outside both vessel portions.

In FIG. 4D, the operator can then introduce inner sheath 30 with the first portion 52 of prosthesis 50 to the end opening 105 of the second portion 100B of the transected body vessel 100. Inner sheath 30 can be removed from the first portion 52 of prosthesis 50 to allow expansion of the first portion 52 of the prosthesis to the expanded configuration to engage along the wall tissue of the second portion 100B of the transected body vessel. For example, handle portion 38 can be pulled from the proximal end of the inner sheath to longitudinally split the inner sheath, such as shown in FIG. 3B. The operator can pull the handle portion from an intermediate portion of the prosthesis, in between the ends of the vessel portions 100A, 100B. As can be seen in the figures, it is preferable for the outer sheath to be removed from one end of the prosthesis toward the intermediate portion of the prosthesis, while the inner sheath is removed from the opposite end toward the intermediate portion of the prosthesis. In other words, the outer sheath can be removed from the distal end of the prosthesis in the proximal direction away from the vessel opening, and the inner sheath can be removed from the proximal end of the prosthesis in the distal direction away from the other vessel opening.

Figure 5:
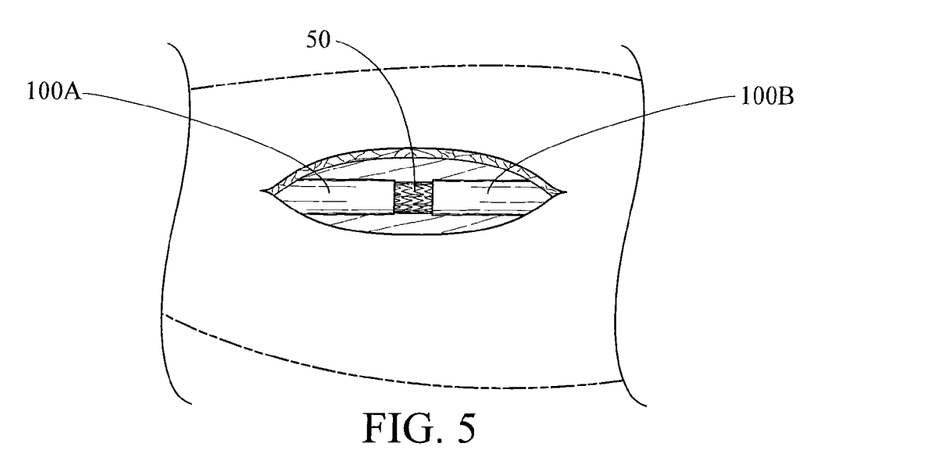
FIG. 5 is a top view of the leg of the patient of FIG. 4, with a repaired body vessel.

In FIG. 4E, prosthesis 50 is fully deployed to bridge the first and second portions 100A, 100B of the transected body vessel 100 to form a passageway for blood flow. The sutures 104 can then be removed. Preferably, portions of the exterior surfaces of the prosthesis sealably engages with the luminal walls of the body vessel to inhibit leakage of blood and to force blood to flow throughout the body vessel during emergency surgery, and particularly to obtain hemostasis while maintaining blood perfusion. FIG. 5 shows prosthesis 50 deployed to connect the two body vessel portions 100A, 100B within the leg of the patient. The prosthesis can be permanently placed within the patient, thereby obviating a need for subsequent surgical intervention.

It can be appreciated by those skilled in the art that the outer sheath can be removed from the prosthesis by other means. For example, the outer sheath can be splittable, having one or more of the features described with respect to inner sheath 30. In addition, it can be appreciated by those skilled in the art that the inner sheath can be removed from the prosthesis by other means. For example, the inner sheath may be bioabsorbable or otherwise dissolvable in response to application of an activation agent configured to rapidly dissolve the inner sheath. Optionally, the inner sheath can be removed by sliding the inner sheath off of the prosthesis.

Although the prosthesis and the deployment system has been described in connection with its primary intended use for repair of vascular trauma, those skilled in the art will appreciate that the device may also be used to repair other traumatic conditions. Non-limiting examples of such conditions include aneurysms, such as abdominal aorta aneurysms, and surgery for tumor removal.

Drawings in the figures illustrating various embodiments are not necessarily to scale. Some drawings may have certain details magnified for emphasis, and any different numbers or proportions of parts should not be read as limiting, unless so-designated in the present disclosure. Those of skill in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

I claim:

1. A deployment system for repair of a body vessel comprising:

a prosthesis having a proximal end and a distal end, a first end portion extending to said proximal end, and a second end portion extending to said distal end, each of said end portions of said prosthesis being radially movable between a circumferentially compressed configuration and a circumferentially expanded configuration, wherein each of the second end portion and the first end portion of the prosthesis are configured to be sequentially introduced into respective opposed second and first openings of a body vessel during deployment such that when deployed the prosthesis provides a fluid conduit between the first and second opposed openings, wherein the first end portion of the prosthesis is introduced into the first opening of the body vessel in a first direction and the second end portion of the prosthesis is introduced into the opposed second opening in a second direction that is different from the first direction;

an inner sheath circumferentially surrounding said first end portion of the prosthesis to retain said first end portion in the circumferentially compressed configuration, leaving said second end portion of the prosthesis uncovered by the inner sheath; an outer sheath having a lumen extending therethrough configured to receive the prosthesis in the compressed configuration, the outer sheath having a delivery position and a deployed position, where, in the delivery position, the outer sheath retains the second end portion of the prosthesis in the circumferentially compressed configuration and the first end portion of the prosthesis with the inner sheath, and, in the deployed position, the outer sheath is entirely removed from the prosthesis and the inner sheath to allow an expansion of the second end portion of the prosthesis to the circumferentially expanded configuration; a proximal handle coupled to the outer sheath, the outer sheath extending proximally past a proximal end of said inner sheath, wherein said proximal end of said inner sheath terminates within said outer sheath distally from said proximal handle, the proximal handle being operable to axially move the outer sheath relative to the prosthesis and the inner sheath between the delivery and deployed positions, such that when the outer sheath is in the deployment position no portion or component of the prosthesis or the inner sheath is connected to the outer sheath or the proximal handle after the outer sheath is entirely removed from the prosthesis and the inner sheath, the prosthesis and the inner sheath being completely disconnected from the outer sheath and the proximal handle after the outer sheath is entirely removed from the prosthesis and the inner sheath, where the inner sheath is removable from the first end portion of the prosthesis by splitting the inner sheath from a proximal end of the inner sheath to a distal end of the inner sheath to allow an expansion of the first end portion of the prosthesis to the circumferentially expanded configuration, independent to the expansion of the second end portion.

2. The system of claim 1, where the prosthesis comprises a tubular graft and one or more self-expanding stent structures attached to the tubular graft.

3. The system of claim 1, where the outer sheath has a tapered distal end to facilitate insertion into an end opening of a body vessel.

4. The system of claim 1, wherein a distal portion of the outer sheath and the distal end of the prosthesis are each sized to fit within a first vessel opening of a transected vessel, and at least a portion of the inner sheath and the proximal end of the prosthesis are each sized to fit within a second vessel end opening of the transected vessel when the distal end of the prosthesis extends into the first vessel opening.

5. The system of claim 1, wherein the prosthesis further comprises an intermediate portion between the first and second end portions, wherein the intermediate portion is allowed to expand after both the second and first end portions have been sequentially allowed to expand.

6. The system of claim 1, wherein the second end portion of the prosthesis is configured to be introduced into the second opening of the body vessel after the first end portion has been introduced into the first opening of the body vessel and after the first end portion of the prosthesis has expanded to the circumferentially expanded configuration.

7. The system of claim 1, further comprising an inner shaft disposed within the outer sheath.

8. The system of claim 7, where the inner shaft comprises an enlarged portion configured to contact the proximal end of the prosthesis in response to axial movement of the outer sheath relative to the enlarged portion.

9. The system of claim 1, the inner sheath comprising a handle portion attached to a proximal portion of the inner sheath, the handle portion configured to facilitate formation of a split in the inner sheath for removal from the first portion of the prosthesis after deployment within said body vessel.

10. The system of claim 9, where the handle portion comprises a length sized to extend beyond the distal end of the inner sheath.

11. The system of claim 9, where the handle portion is configured to axially split the inner sheath.

12. A method of delivering a prosthesis for intraoperative repair of a transected body vessel, comprising:

providing a deployment system including a prosthesis having a proximal end and a distal end, a first end portion extending to said proximal end, and a second end portion extending to said distal end, said prosthesis being radially movable between a compressed configuration and an expanded configuration, an inner sheath configured to circumferentially surround said first end portion of the prosthesis for selectively retaining said first end portion in the compressed configuration, leaving said second end portion of the prosthesis uncovered by the inner sheath, an outer sheath having a lumen extending therethrough configured to receive the prosthesis in the compressed configuration, the outer sheath retaining the second end portion of the prosthesis in the compressed configuration and the first end portion of the prosthesis with the inner sheath, a proximal handle coupled to the outer sheath, the outer sheath extending proximally past a proximal end of said inner sheath, wherein said proximal end of said inner sheath terminates within said outer sheath distally from said proximal handle;

inserting a distal end of the outer sheath of the deployment system into a first end opening of said transected body vessel, and positioning the system so that a length of the second end portion of the prosthesis is within a first vessel portion;

axially removing the outer sheath entirely from the prosthesis and the inner sheath by operating the proximal handle to move the outer sheath proximally relative to the prosthesis and the inner sheath, the prosthesis thereby allowing an expansion of the second end portion of the prosthesis to the expanded configuration so that the second end portion of prosthesis engages along a vessel wall of the first vessel portion, no portion or component of the prosthesis or the inner sheath being connected to the outer sheath or the proximal handle after the outer sheath is entirely removed from the prosthesis and the inner sheath, the prosthesis and the inner sheath being completely disconnected from the outer sheath and the proximal handle after the outer sheath is entirely removed from the prosthesis and the inner sheath;

thereafter inserting a length of the first end portion of the prosthesis with the inner sheath into a second end opening of said transected body vessel; and removing the inner sheath from the first end portion of the prosthesis to allow an expansion of the first end portion of the prosthesis to the expanded configuration so that the first end portion engages along a vessel wall of a second vessel portion, and the prosthesis provides a fluid conduit between the first and second vessel portions of the transected body vessel.

13. The method of claim 12, further comprising providing a blocker disposed within the lumen of the outer sheath proximal to the prosthesis, where, in response to axially moving the outer sheath relative to the blocker, the blocker contacts the proximal end of the prosthesis.

14. The method of claim 12, where the outer sheath is removed from the prosthesis in a first direction toward an intermediate portion of the prosthesis away from the prosthesis, and the inner sheath is removed from the first end portion of the prosthesis in a second direction, opposite the first direction, toward the intermediate portion of the prosthesis, and the intermediate portion of the prosthesis radially expands subsequent to radial expansion of the first and second end portions of the prosthesis.

15. A deployment system for vascular repair of a transected body vessel that defines first and second vessel end openings, comprising:
a self-expanding prosthesis having a proximal end and a distal end, a first end portion extending to said proximal end, and a second end portion extending to said distal end, each of said first and second end portions of the prosthesis being radially movable between a circumferentially compressed configuration and a circumferentially expanded configuration, wherein each of the second end portion and the first end portion are configured to be sequentially introduced into respective opposed second and first vessel end openings of a body vessel during deployment such that when deployed the prosthesis provides a fluid conduit between the first and second vessel end openings, wherein the first end portion of the prosthesis is introduced into the first vessel opening of the transected body vessel in a first direction and the second end portion of the prosthesis is introduced into the second vessel opening of the transected body vessel in a second direction that is different than the first direction;
an inner sheath positioned to circumferentially surround said first end portion of the prosthesis to leave said second end portion of the prosthesis uncovered by the inner sheath, where the inner sheath is configured to selectively retain said first end portion of the prosthesis in the circumferentially compressed configuration;
an outer sheath disposed around the prosthesis to retain the second end portion of the prosthesis in the circumferentially compressed configuration and to surround the inner sheath with the first end portion of the prosthesis in the circumferentially compressed configuration;
an inner shaft disposed within the outer sheath, wherein the inner shaft directly contacts the proximal end of the prosthesis; and
a proximal handle coupled to the outer sheath and the inner shaft, the outer sheath extending proximally past a proximal end of said inner sheath, wherein said proximal end of said inner sheath terminates within said outer sheath distally from said proximal handle, the proximal handle being operable to axially move the outer sheath and inner shaft relative to the prosthesis and the inner sheath,
where a distal portion of the outer sheath and the distal end of the prosthesis are each sized to fit within the second vessel end opening of a transected vessel, and the outer sheath is entirely removable from the prosthesis and the inner sheath to allow a first expansion of the second end portion of the prosthesis to the circumferentially expanded configuration within the second vessel end opening of the transected body vessel, no portion or component of the prosthesis or the inner sheath being connected to the outer sheath or the proximal handle after the outer sheath and inner shaft are entirely removed from the prosthesis and the inner sheath, the prosthesis and the inner sheath being completely disconnected from the outer sheath and inner shaft and the proximal handle after the outer sheath is entirely removed from the prosthesis and the inner sheath,
where at least a portion of the inner sheath and the proximal end of the prosthesis are each sized to fit within the second vessel end opening of the transected vessel when the distal end of the prosthesis extends into the first vessel end opening, and the inner sheath is removable from the first end portion of the prosthesis to allow a second expansion, independent to the first expansion, of the first end portion to the circumferentially expanded configuration at the second of the vessel end openings of said transected body vessel.

16. The system of claim 15, where the outer sheath is slidably removed from the prosthesis in a proximal direction toward the proximal end of the prosthesis and away from the distal end of the prosthesis to allow radial circumferential expansion of the second end portion of the prosthesis, and the inner sheath is a splittable sheath capable of being longitudinally split in a manner to allow radial circumferential expansion of the first end portion of the prosthesis.

17. The system of claim 15, wherein the prosthesis further comprises an intermediate portion between the first and second end portions, wherein the intermediate portion is allowed to expand after both the second and first end portions have been sequentially allowed to expand.

18. The system of claim 15, wherein the second end portion of the prosthesis is configured to be introduced into the second vessel opening of the transected body vessel after the first end portion has been introduced into the first vessel opening of the transected body vessel and after the first end portion of the prosthesis has expanded to the circumferentially expanded configuration.

19. The system of claim 15, where the outer sheath is configured to be removed from the prosthesis in a third direction opposite the second direction toward an intermediate portion of the prosthesis away from the distal end of the prosthesis.

20. The system of claim 19, where the inner sheath is configured to be removed from the first end portion of the prosthesis in a fourth direction, opposite the first direction, toward the intermediate portion of the prosthesis away from the proximal end of the prosthesis, whereby radial expansion of the intermediate portion of the prosthesis is subsequent to radial expansion of the first and second end portions of the prosthesis.

21. A deployment system for repair of a body vessel comprising:
a prosthesis having a proximal end and a distal end, a first end portion extending to said proximal end, and a second end portion extending to said distal end, each of said end portions of said prosthesis being radially movable between a compressed configuration and an expanded configuration, wherein each of the second end portion and the first end portion are configured to be sequentially introduced through an open region of the body vessel that has been at least partially transected into respective second and first openings positioned on opposing sides of the open region during deployment such that the prosthesis provides a fluid conduit between the first and second opposed openings;

an inner sheath circumferentially surrounding said first end portion of the prosthesis to retain said first end portion in the compressed configuration, leaving said second end portion of the prosthesis uncovered by the inner sheath;

an outer sheath having a lumen extending therethrough configured to receive the prosthesis in the compressed configuration, the outer sheath having a delivery position and a deployed position, where, in the delivery position, the outer sheath retains the second end portion of the prosthesis in the compressed configuration and the first end portion of the prosthesis with the inner sheath, and, in the deployed position, the outer sheath is removed from the prosthesis and the inner sheath to allow an expansion of the second end portion of the prosthesis to the circumferentially expanded configuration, a proximal handle coupled to the outer sheath, the outer sheath extending proximally past a proximal end of said inner sheath, wherein said proximal end of said inner sheath terminates within said outer sheath distally from said proximal handle, the proximal handle being operable to axially move the outer sheath relative to the prosthesis and the inner sheath between the delivery and deployed positions, wherein the inner sheath is removable from the first end portion of the prosthesis by splitting the inner sheath from a proximal end of the inner sheath to a distal end of the inner sheath to allow an expansion of the first end portion of the prosthesis to the circumferentially expanded configuration, independent to the expansion of the second end portion.

22. The system of claim 21, wherein the prosthesis further comprises an intermediate portion between the first and second end portions, wherein the central portion is allowed to expand after both the second and first end portions have been sequentially allowed to expand.

23. The system of claim 21, wherein the second end portion of the prosthesis is configured to be introduced into the second opening of the body vessel after the first end portion has been introduced into the first opening of the body vessel and after the first end portion of the prosthesis has expanded to the expanded configuration.

24. The system of claim 21, the inner sheath comprising a handle portion attached to a proximal portion of the inner sheath, the handle portion configured to facilitate formation of a split in the inner sheath for removal from the first portion of the prosthesis after deployment within said body vessel.

25. The system of claim 24, where the handle portion comprises a length sized to extend beyond the distal end of the inner sheath.

26. The system of claim 24, where the handle portion is configured to axially split the inner sheath.

* * * * *